United States Patent [19]
McGuinness

[11] Patent Number: 6,066,169
[45] Date of Patent: May 23, 2000

[54] EXPANDABLE STENT HAVING ARTICULATED CONNECTING RODS

[75] Inventor: Colm McGuinness, Galway, Ireland

[73] Assignee: Ave Connaught, Dublin, Ireland

[21] Appl. No.: 09/088,907

[22] Filed: Jun. 2, 1998

[51] Int. Cl.[7] .................................................. A61F 2/06
[52] U.S. Cl. ........................................................ 623/1.16
[58] Field of Search ......................... 623/1, 12, 1.16, 623/1.15

[56] References Cited

U.S. PATENT DOCUMENTS

| | | |
|---|---|---|
| 4,319,363 | 3/1982 | Ketharanathan . |
| 4,604,762 | 8/1986 | Robinson . |
| 4,647,416 | 3/1987 | Seiler, Jr. et al. . |
| 4,649,922 | 3/1987 | Wiktor . |
| 4,733,665 | 3/1988 | Palmaz . |
| 4,739,762 | 4/1988 | Palmaz . |
| 4,760,849 | 8/1988 | Kroff . |
| 4,776,337 | 10/1988 | Palmaz . |
| 4,800,882 | 1/1989 | Gianturco . |
| 4,830,003 | 5/1989 | Wolff et al. . |
| 4,856,516 | 8/1989 | Hillstead . |
| 4,886,062 | 12/1989 | Wiktor . |
| 4,994,071 | 2/1991 | MacGregor . |
| 5,015,253 | 5/1991 | MacGregor . |
| 5,019,090 | 5/1991 | Pinchuk . |
| 5,133,732 | 7/1992 | Wiktor . |
| 5,161,547 | 11/1992 | Tower . |
| 5,217,483 | 6/1993 | Tower . |
| 5,282,823 | 2/1994 | Schwartz et al. . |
| 5,282,824 | 2/1994 | Gianturco . |
| 5,304,200 | 4/1994 | Spaulding . |
| 5,314,472 | 5/1994 | Fontaine . |
| 5,330,500 | 7/1994 | Song . |
| 5,354,309 | 10/1994 | Schnepp-Pesch et al. . |
| 5,370,683 | 12/1994 | Fontaine . |
| 5,405,377 | 4/1995 | Cragg . |
| 5,443,498 | 8/1995 | Fontaine . |
| 5,443,500 | 8/1995 | Sigwart . |
| 5,449,373 | 9/1995 | Pinchasik et al. . |
| 5,456,711 | 10/1995 | Hudson . |
| 5,476,508 | 12/1995 | Amstrup . |
| 5,540,713 | 7/1996 | Schnepp-Pesch et al. . |
| 5,545,210 | 8/1996 | Hess et al. . |
| 5,591,197 | 1/1997 | Orth et al. . |
| 5,593,442 | 1/1997 | Klein . |
| 5,607,442 | 3/1997 | Fischell et al. . |
| 5,632,771 | 5/1997 | Boatman et al. . |
| 5,636,641 | 6/1997 | Fariabi et al. . |
| 5,665,115 | 9/1997 | Cragg . |
| 5,667,523 | 9/1997 | Bynon et al. . |
| 5,697,971 | 12/1997 | Fischell et al. . |
| 5,843,164 | 12/1998 | Frantzen et al. ............................ 623/1 |
| 5,906,640 | 5/1999 | Penn et al. ................................. 623/1 |
| 5,922,020 | 7/1999 | Klein et al. ................................ 623/1 |
| 5,925,061 | 7/1999 | Ogi et al. ................................... 623/1 |

FOREIGN PATENT DOCUMENTS

| | | |
|---|---|---|
| 0 346 564 B1 | 12/1991 | European Pat. Off. . |
| 0 744 164 A1 | 11/1996 | European Pat. Off. . |
| WO 92/09246 | 6/1992 | WIPO . |
| WO 94/00179 | 1/1994 | WIPO . |
| WO 95/26695 | 10/1995 | WIPO . |
| WO 96/39102 | 12/1996 | WIPO . |
| WO 96/41590 | 12/1996 | WIPO . |
| WO 96/41591 | 12/1996 | WIPO . |
| WO 97/14375 | 4/1997 | WIPO . |
| WO 97/25937 | 7/1997 | WIPO . |
| WO 97/26840 | 7/1997 | WIPO . |
| WO 97/32543 | 9/1997 | WIPO .................................. 623/1.16 |

*Primary Examiner*—David H. Willse
*Assistant Examiner*—Suzette J. Jackson
*Attorney, Agent, or Firm*—Sterne, Kessler, Goldstein & Fox P.L.L.C.

[57] ABSTRACT

The invention includes systems and methods for providing stents having expandable cylindrical elements that are connected by articulated arms and connecting rods. These stents are understood to reduce the shortening that can occur as the stent is expanded from a first radial dimension to a second radial dimension.

10 Claims, 5 Drawing Sheets

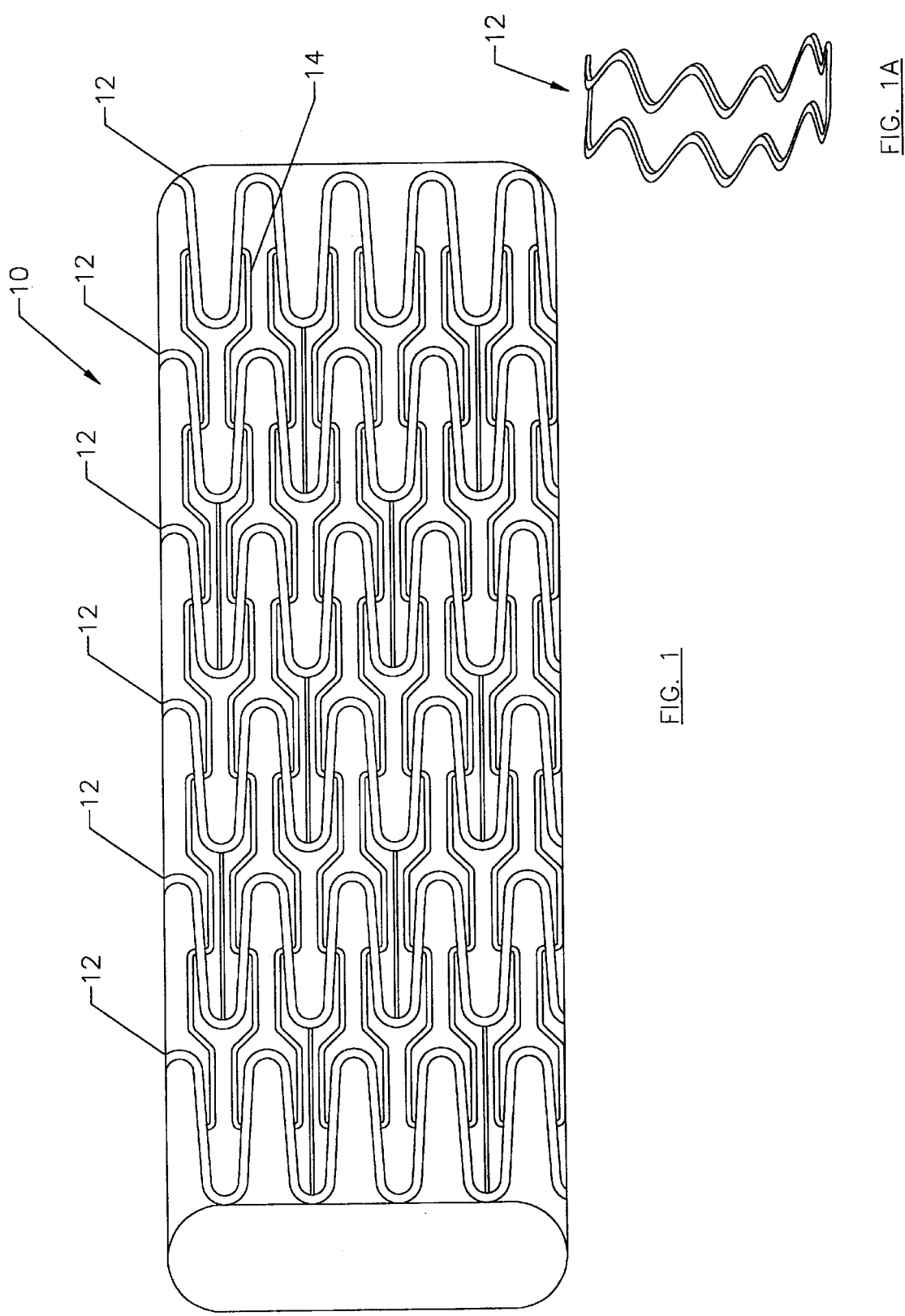

EXPANDABLE STENT HAVING ARTICULATED CONNECTING RODS

FIELD OF THE INVENTION

The invention relates to an endovascular stent for transluminal delivery to a body lumen, such as a blood vessel and, more particularly, to an endovascular stent that includes a plurality of cylindrical elements joined together by connecting elements formed as articulated arms. The stents can comprise a deformable material, thereby allowing expansion of the stent by action of an inflatable balloon mounted at the end of a catheter.

BACKGROUND OF THE INVENTION

It is expected that there will be more than 500,000 balloon angioplasty procedures performed worldwide this year. For a typical angioplasty procedure, the treating physician will identify an obstructed vessel, such as a coronary artery blocked by plaque build-up, and then inflate a small balloon within the vessel at the site of the obstruction. The inflating balloon dilates the obstructed vessel and restarts or increases blood flow through that vessel.

Balloon angioplasty has been remarkably successful at opening blocked vessels and restoring normal levels of blood flow. However, despite the initial success of the angioplasty treatment, long term efficacy is hampered by a tendency of treated vessels to re-close shortly after the initial procedure. It is understood that in thirty to fifty percent of cases, successfully treated patients will suffer within three to six months a reclosure of the dilated vessel at the site of the initial obstruction. Lincoff et al., Local Drug Delivery for the Prevention of Restenosis, Circulation, vol. 90, No. 4, (October 1994). The cause of restenosis is complex and still under study, however, it appears that restenosis results, at least in some cases, from thrombus formation. Whatever the reason restenosis is a significant factor in patient recovery and a common cause of repeat balloon angioplasty or surgical intervention.

One approach to dealing with the problem of restenosis is to maintain a passage through the artery with an endovascular stent. The stent is a generally tubular device which is placed inside the blood vessel after balloon angioplasty has been completed. The stent has sufficient strength and resiliency to resist restenosis and to maintain a passage through the vessel.

U.S. Pat. No. 4,733,665, issued Mar. 29, 1988 to Palmaz, discloses a vascular stent comprising an expandable tube. The stent is positioned over an inflatable balloon secured to a catheter and is advanced to the stenosed region. The balloon is inflated, thereby expanding the stent into contact with the vessel wall. The elastic limit of the wire mesh is exceeded when the balloon is expanded, so that the stent retains its expanded configuration. U.S. Pat. No. 4,503,569, issued Mar. 12, 1985 to Dotter, discloses a shape memory alloy stent that is advanced to a stenosed region on a catheter. The stent has the form of a coil spring. After positioning, the stent is heated with a hot fluid causing the shape memory alloy to expand into contact with the blood vessel.

Although these known stent designs can perform well, there are cases in which the stent falls to prevent restenosis. In these cases the problem of vessel obstruction is compounded by the existence of a stent that is now fixed within the vessel. Additionally, the success of a stent to prevent restenosis depends in part on the ability of the stent to span across the full length of the lesion being treated. To the extent that the stent falls to span the site of the obstruction, restenosis can occur, resulting in a reclosure of the vessel, and the need for further surgical intervention. Unfortunately, with some stent designs the radial expansion achieved by inflating the balloon leads to coincident foreshortening of the stent, often resulting in the failure of the stent to span the lesion being treated.

Accordingly, it is a general object of the invention to provide improved endovascular stents.

It is a further object of the invention to provide an endovascular stent that reduces the likelihood of failure due to tissue growth through the sides of the stent.

It is yet another object of the invention to provide an endovascular stent which is delivered to a selected site in a blood vessel and which is released from the inflatable balloon and attached to the blood vessel by the application of energy through the wall of the balloon.

SUMMARY OF THE INVENTION

Various embodiments of the invention are described herein, including intraluminal stents and methods for performing angioplasty that employ intraluminal stents suitable for being placed within a body lumen, such as a cardiac artery, for treating a lesion or other obstruction within the artery. In one embodiment, the stents include a plurality of cylindrical elements comprising sinusoidally-shaped coils which are interconnected by a set a connecting elements, in which some of the connecting elements are formed as articulated arms, and others of the connecting elements are formed as substantially straight connecting rods. The connecting elements interconnect the cylindrical elements to provide an expandable stent that has reduced foreshortening upon expansion, and thereby provides improved performance.

In one aspect, the invention is understood as an expandable intraluminal stent for implanting in a body lumen. The stent can comprise a first cylindrical element that is adapted for expanding from a first radial dimension to a second radial dimension, a second cylindrical element adapted for expanding from a first radial dimension to a second radial dimension, and being positioned adjacent and spaced away from the first cylindrical element to define a longitudinal axis extending through the first and second cylindrical elements. The stent further includes an articulated arm that joins the first and second cylindrical elements as well as a substantially straight connecting rod that joins the first and second cylindrical elements, thereby providing a stent that can respond to a force acting radially outward to expand the stent from the first radial dimension to the second radial dimension.

In one embodiment, the stents include cylindrical elements that can have a shape which facilitates expansion. In one example, the cylindrical elements have a sinusoidal shape with a plurality of peaks and troughs. The sinusoidal shape of the cylindrical elements is understood to allow for the expansion of the cylindrical elements from a first radial diameter to a second radial diameter. However, it will be understood by one of ordinary skill in the art, that the cylindrical elements can be alternatively configured for expansion and, for example, can have a zig-zag shape formed from inter-connected V-shaped elements or any other configuration suitable for facilitating the radial expansion of the cylindrical elements. In these embodiments, the articulated arms can join to the cylindrical elements at a point located between a peak and a trough, and typically substantially mid-way between a peak and trough.

Optionally, the articulated arms can include a section, such as a curved section, which increases the scaffold density of the stent's outer wall to provide greater coverage of the tissue wall of a body lumen, such as the tissue wall of a cardiac artery.

In one particular embodiment, each of the cylindrical elements is configured as a sinusoidal coil and the connecting rods extend between the peaks on a first cylindrical element to the peaks on a second cylindrical element.

In a further embodiment, the stents can include a graft which is formed about the peripheral surface defined by the cylindrical elements of the stent. In this way, the invention is understood to provide a stent-graph suitable for implantation within a body lumen. The stents and stent-graphs described herein, typically provide stents wherein the overall length of the stent in a first radial dimension is substantially the same as the overall length of the stent in the second larger radial dimension. The stents described herein can be formed from a substantially tubular body of a material, such as a biocompatible material like 316 stainless steel. Alternatively, the inter-luminal stents described herein can be formed from a substantially flat sheet of material which is milled and then rolled into a cylindrical body and welded into a tube. The tubular bodies are milled or etched to have a pattern that appears as a set of cylindrical elements, typically each of which has a sinusoidal shape, joined by connecting elements which comprise articulated arms and substantially straight connecting rods. The exterior surface of the stents described herein have apertures extending therethrough and typically the apertures are dimensionally adapted to provide wall coverage substantially capable of reducing the likelihood that biological material from the interior tissue wall of the lumen would extend into the interior of the tubular stent. This is understood to reduce the likelihood of thrombosis and later narrowing or closing of the body lumen.

In another aspect, the invention is understood as methods for forming an expandable intraluminal stent. These methods can comprise the steps of providing a body of material, such as a sheet or tube of stainless steel, and cutting a pattern into the body that provides a first cylindrical element adapted for expanding from a first radial dimension to a second radial dimension, and a second cylindrical element adapted for expanding from a first radial dimension to a second radial dimension. The pattern disposes the second cylindrical element adjacent and spaced away from the first cylindrical element. The methods can include the additional steps of forming articulated arms between the first and second cylindrical elements and forming a substantially straight connecting rod between the first and second cylindrical elements, whereby the connecting rods and articulated arms inter-connect the separate and adjacent cylindrical elements.

The process for forming the stents described herein, can include the steps of laser milling, chemical etching, a tubular body, or sheet of material. However, any suitable technique can be employed for milling a biologically compatible material to form the tubular stents described herein. Moreover, it will be understood by one of ordinary skill in the art that the cylindrical elements can have circular, or elliptical cross-sections, or cross-sections of any other suitable geometry.

BRIEF DESCRIPTION OF THE ILLUSTRATED EMBODIMENTS

For a better understanding of the invention together with objects, advantages and capabilities thereof, reference is made to the accompanying drawings in which like reference numbers refer to like elements:

FIG. 1 depicts a stent having a plurality of connecting elements including articulated arms and substantially straight connecting rods;

FIG. 1A depicts a perpective view of a cylindrical element of a stent;

DETAILED DESCRIPTION OF THE ILLUSTRATED EMBODIMENTS

Figures 2A, 2B:
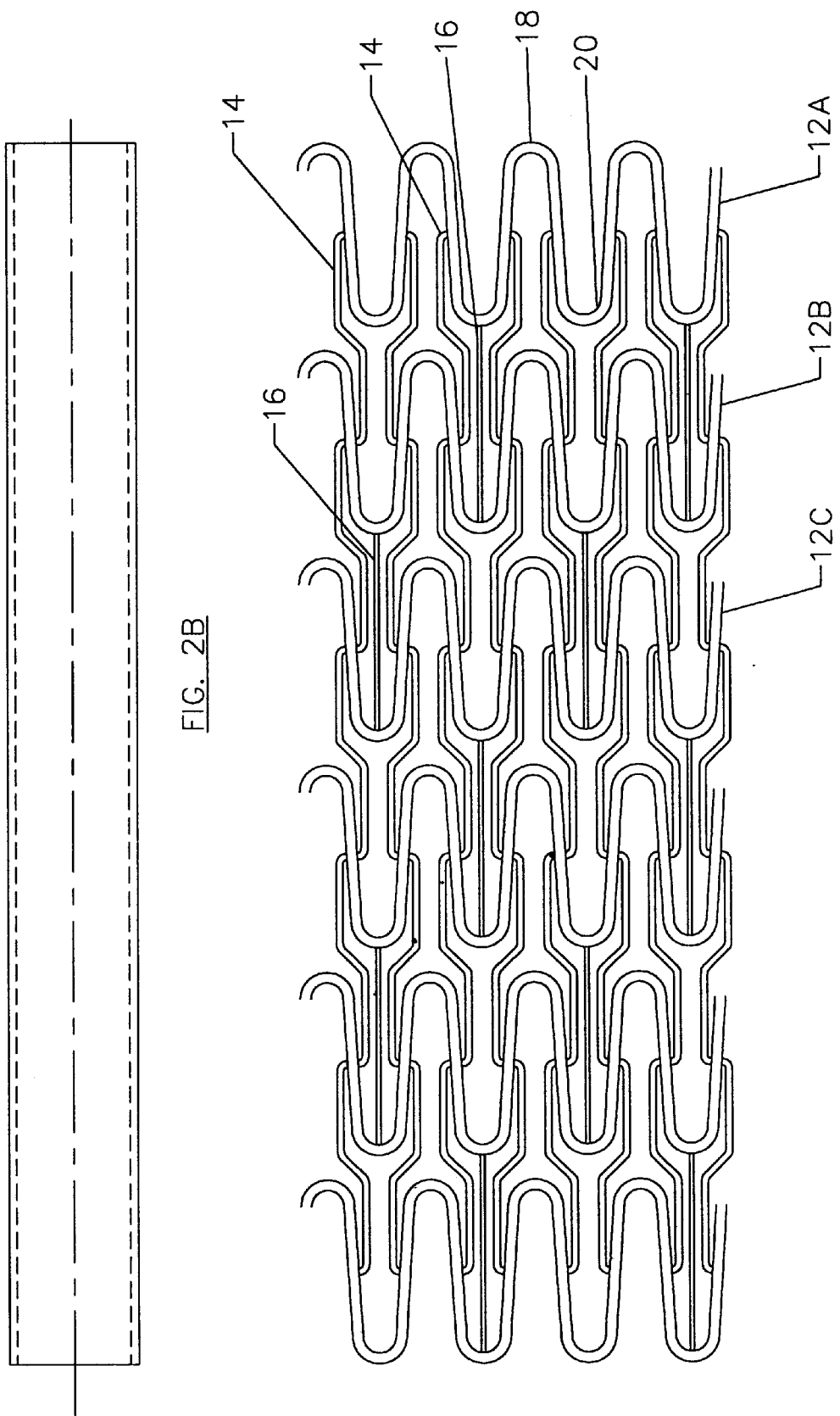
FIGS. 2A and 2B depict in greater detail a tubular stent having a set of adjacent coils joined by a plurality of connecting elements including articulated arms and connecting rods.

The invention will now be described with reference to certain illustrated embodiments that show stents suitable for delivering and implantation within a body lumen, such as a cardiac artery. However, it will be understood that the invention can be realized in other embodiments and for other applications, including bifurcated stents, and stent-graft endoprostheses, including stent-grafts for treating aortic aneurysms.

FIG. 1 depicts an intravascular stent 10 including cylindrical elements 12, articulated arms 14, and connecting rods 16. The depicted stent 10 has a generally tubular shape with an interior lumen 17 that is dimensionally adapted for receiving a balloon mounted on the end of a balloon catheter and for being delivered through a patient's vascular system to the site of a lesion or obstruction. The depicted stent 10 is an expandable intravascular stent that can be radially expanded from a first radial diameter to a second radial diameter, wherein in the second radial diameter the stent 10 abuts against the interior tissue wall of a vessel and supports the vessel to reduce the likelihood of collapse or obstruction.

The depicted stent 10 can be milled from a tubular body of biocompatible material, such as a seamless tube of 316 stainless steel. The stent 10 is approximately 15 millimeters in length, with an outer diameter of 1.6 millimeters and an inner diameter of approximately 1.4 millimeters. The stainless steel material is inelastically deformable such that the radial force of an expanding balloon can increase the outer diameter of the stent 10 from approximately 1.6 millimeters to the internal diameter of the vessel. Typically, the biocompatible material is sufficiently rigid in its expanded condition to avoid collapse due to the force of the vessel wall acting on the exterior surface of the stent.

FIG. 2A depicts in greater detail the interconnection of the cylindrical elements 12, articulated arms 14 and connecting rods 16 of the stent depicted in FIG. 1. FIG. 2A depicts a set of six serpentine cylindrical elements 12 disposed adjacent to each other and interconnected by the articulated arms 14 and connecting rods 16. Each cylindrical element 12 comprises a coil having coil 12 has a serpentine, or sinusoidal, structure having a plurality of peaks 18 and troughs 20. Each adjacent pair of cylindrical elements, such as the adjacent pair 12a and 12b, depicted in FIG. 2A are interconnected such that articulated arms 14 join to a first cylindrical elements, such as cylindrical elements 12a, at the midpoint between one of the peaks and troughs of the celendrical elements 12a and the other end of the articulated arm 14 joins at the midpoint between a peak and a trough of the adjacent cylindrical elements 12b. For purposes of describing the pattern depicted by FIG. 2A, it can be understood that each of the cylindrical elements 12 is composed of a set U-shaped structures that are seamlessly interconnected and facing alternating directions. With this understanding, it can be seen that each of the individual U-shaped members depicted in FIG. 2A are interconnected by a pair of articulated arms 14 to an adjacent U-shaped member of an adjacent cylindrical elements. FIG. 2A further depicts that the connecting rods 16 also act to join adjacent cylindrical elements, such as 12a and 12b, by joining either end of the connecting rod 16 to a respective one of the sinusoidal cylindrical elements 12a and 12b. In the depicted embodiment, the connecting rods 16 are formed between the cylindrical elements 12a and 12b, to what can be understood as adjacent peaks of the sinusoidal coils 12a and 12b. FIG. 2A further depicts that the connecting rods are interdisposed within the stent pattern, connecting alternate pairs of adjacent troughs. It is further shown by FIG. 2A that the alternating pattern of the connecting rods 16 can be offset between adjacent pairs of sinusoidal coils.

FIG. 2A also depicts that the articulated arms 14 and the connecting rods 16, along with the cylindrical elements 12, define an exterior wall of the stent 10. When expanded, the exterior wall buts against the vessel wall of the lumen being treated. It will be appreciated by one of ordinary skill, that the articulated arms 14 and the connecting rods 16 cooperate to provide improved wall coverage of the vessel wall. This is understood to provide a treating surgeon with greater confidence that tissue flaps hanging from the vessel wall will be held back against the tissue wall and prevented from extending into the interior lumen. By reducing the likelihood that tissue extends into the interior lumen, it is understood that clotting within the lumen may be reduced. To this end, the connecting rods and articulated arms define an exterior surface with apertures sized to reduce the likelihood that tissue flaps will extend through the apertures and into the interior lumen.

It should be understood that FIG. 2A provides a plane view of the outer cylindrical wall of the stent 10. Specifically, FIG. 2A depicts the exterior surface of the tubular stent as a flat surface, as if the tubular stent was cut on a seam extending along its longitudinal axis and unrolled and made flat. The length of the stent 10 that extends along the longitudinal axis is still approximately 15 mm. The width of the pattern depicted in FIG. 2A is approximately 5 mm, which is the unrolled circumference of the stent 10 depicted in FIG. 1 that has an outer diameter of approximately 1.6 mm. Each of the cylindrical elements is approximately 2.25 mm wide. The thickness of the metal forming the serpentine coils, and connecting elements is the same as the thickness of the metal tube from which the coils and connecting elements are cut. For the stent 10 depicted in FIG. 1, the thickness of the metal is approximately 0.2 mm.

FIG. 2B shows in outline the tubular structure of the stent depicted in FIG. 1. Specifically, FIG. 2B shows that the patterned exterior wall of the stent defines a sidewall that surrounds an interior lumen. The sidewall has a thickness of about 0.1 mm and can be circular in cross-section with an interior diameter of about 1.4 mm.

Figure 3:
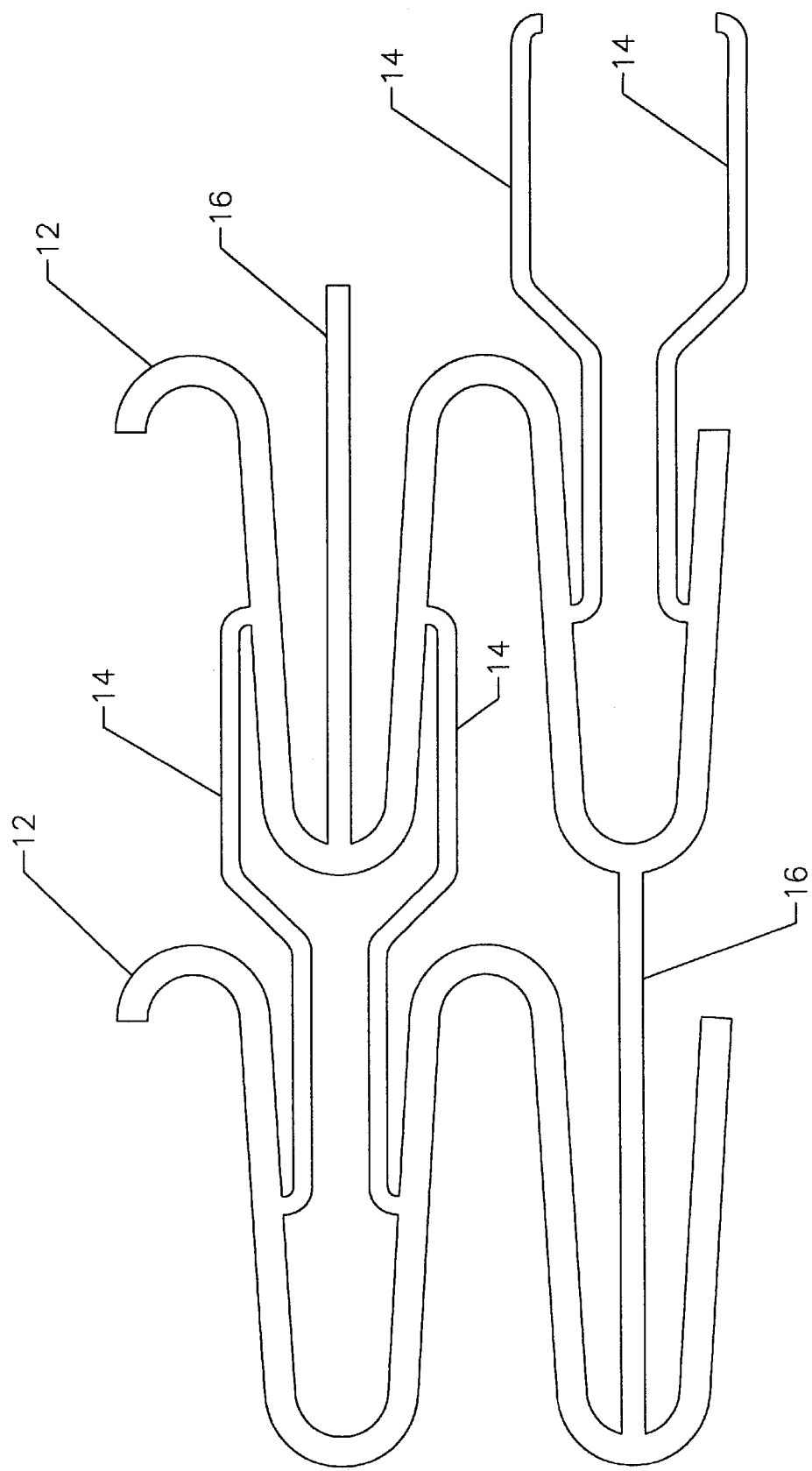
FIG. 3 depicts an alternate technique for providing articulated arms and connecting rods to join the cylindrical elements of a stent.

FIG. 3 depicts a further alternative embodiment. Specifically, FIG. 3 depicts a pattern for the sidewall of a stent that includes cylindrical elements 12 which are interconnected by articulated arms 14 and connecting rods 16. As shown in FIG. 3, the articulated arms 14 are employed to connect alternating pairs of adjacent U-shaped elements of the cylindrical elements 12. Accordingly, in the embodiment of FIG. 3, every other U-shaped portion of the cylindrical elements 12 are connected by a pair of articulated arms. Additionally, as shown by FIG. 3, the articulated arms 14 interconnecting the different U-shaped elements are staggered between adjacent pairs of sinusoidal coils. The connecting rods 16 depicted in FIG. 3 are similarly disposed as those shown in FIG. 2 wherein each connecting rod 16 connects between the peaks of two adjacent U-shaped elements with an alternating pattern of connected U-shaped elements and unconnected U-shaped elements. Accordingly, in the embodiment of FIG. 3, the stent employs a reduced number of articulated arms 14 for joining adjacent cylindrical elements 12.

The depicted articulated arms 14 have two segments that extend substantially longitudinally, and which are joined together by a third segment that extends between the two longitudinal sections and which has an inclined disposition. In the illustrated embodiment, the articulated arms 14 connect the exterior portion of one U-shaped element to the interior portion of another U-shaped element. It will be understood that the depicted articulated arm 14 is only one embodiment of such an arm and that other embodiments can also be employed, including arms with more gentle curves between segments, with greater or fewer segments, including an arm formed as a unitary body.

One method for forming a stent, such as the stent 10 depicted in FIG. 1 can include the steps of providing a flat sheet of biocompatible material, such as stainless steel 316, and laser milling the flat sheet of material to form the pattern depicted in FIG. 2A. After milling the pattern into the sheet of material, the upper and lower edges of the milled sheet can be joined together by rolling the sheet of material about its longitudinal axis to form a cylinder. The two edges of the rolled sheet can be joined by welding, or another suitable method for forming the stent as depicted in FIG. 1. The sheet could also be etched. Alternatively, the stent depicted in FIG. 1 can be formed from a piece of tubing comprising a biocompatible material, again such as 316 stainless steel. The stainless steel tube can be a seamless tube which can be laser milled or chemically etched to form the pattern depicted in FIG. 2A.

The expansion properties of stainless steel are understood to make it an acceptable material for the stent 10. However, other materials are contemplated which include combinations of stainless steel and polymer materials. Further, other suitable materials might include tungsten, platinum, gold, or combinations of these materials in forming the stent 10. As described above, the stent 10 can be formed from a flat sheet of material or from a single piece of tubing by chemically etching, laser cutting, or using an electronic discharge machine. Although any of these techniques can be employed for forming stents according to the invention, it will be understood that any techniques suitable for forming a stent as depicted and described herein can be practiced with the invention without departing from the scope thereof.

Figure 4:
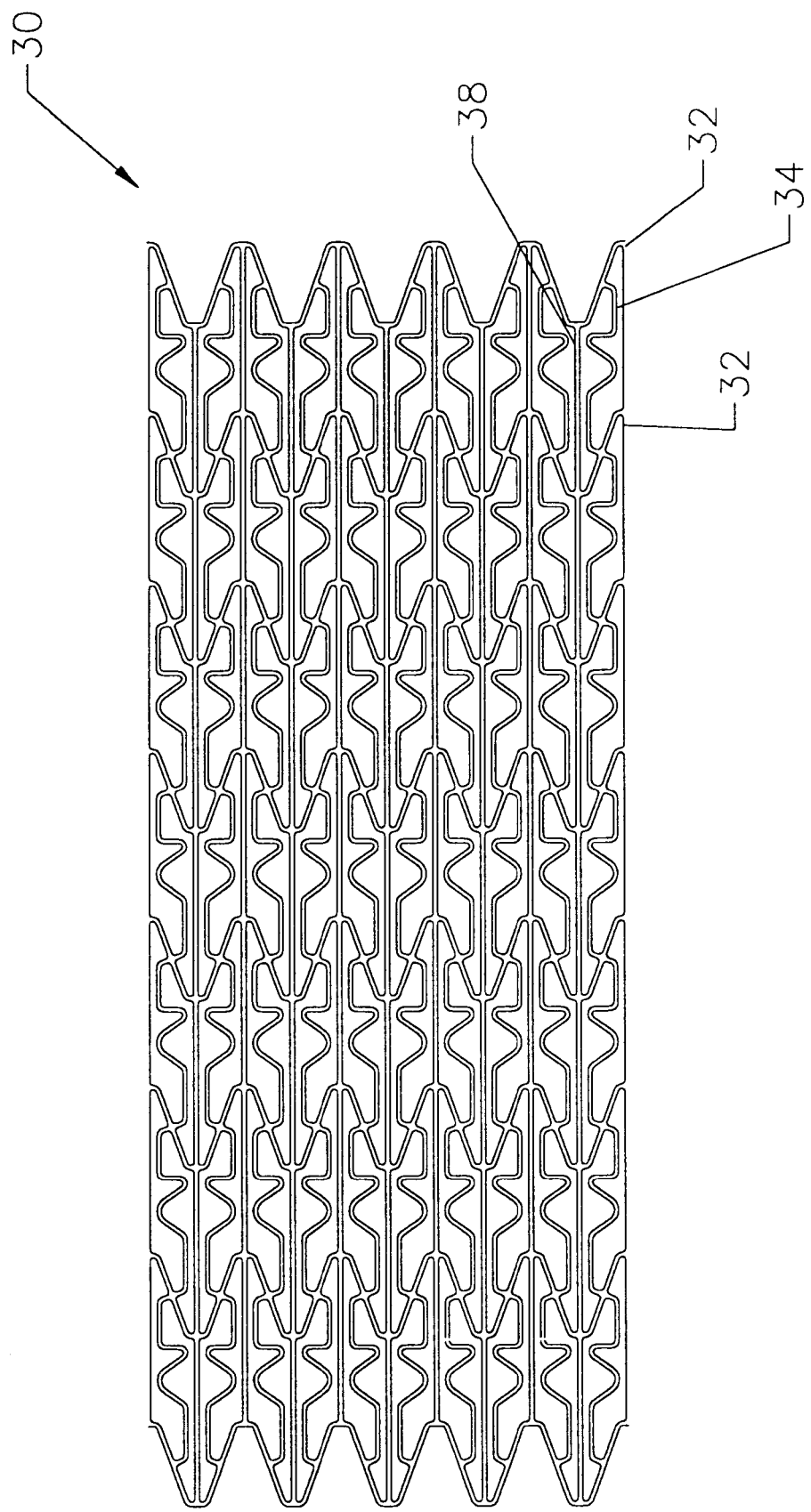
FIG. 4 depicts a further alternative embodiment including articulated arms having curved sections disposed therein.

FIG. 4 depicts a further alternative embodiment of a stent that includes articulated arms and substantially straight connecting members that are formed between adjacent sinusoidal cylindrical elements to provide a stent suitable for implanting within a body lumen. The stent 30 depicted in FIG. 4 includes a plurality of cylindrical elements 32 each of which are interconnected to an adjacent cylindrical elements by articulated arms 34 and substantially straight connecting rods 38. The stent 30 as depicted in FIG. 4 is approximately 15 mm in length, with an inner diameter of approximately of 1.6 mm and an outer diameter of 1.8 mm. The stent 30 can be formed of a biocompatible material, such as stainless steel 316 and can be formed from a seamless tube made of stainless steel by any of the methods described above. Again, as with the above-embodiments, the articulated arms and connecting rods reduce forshortening of the stent as it expands from a first radial dimension, to a second larger radial dimension. Accordingly, the overall length of the stent in the first radial dimension is substantially the same as the overall length of the stent in the second radial dimension.

Figure 5:
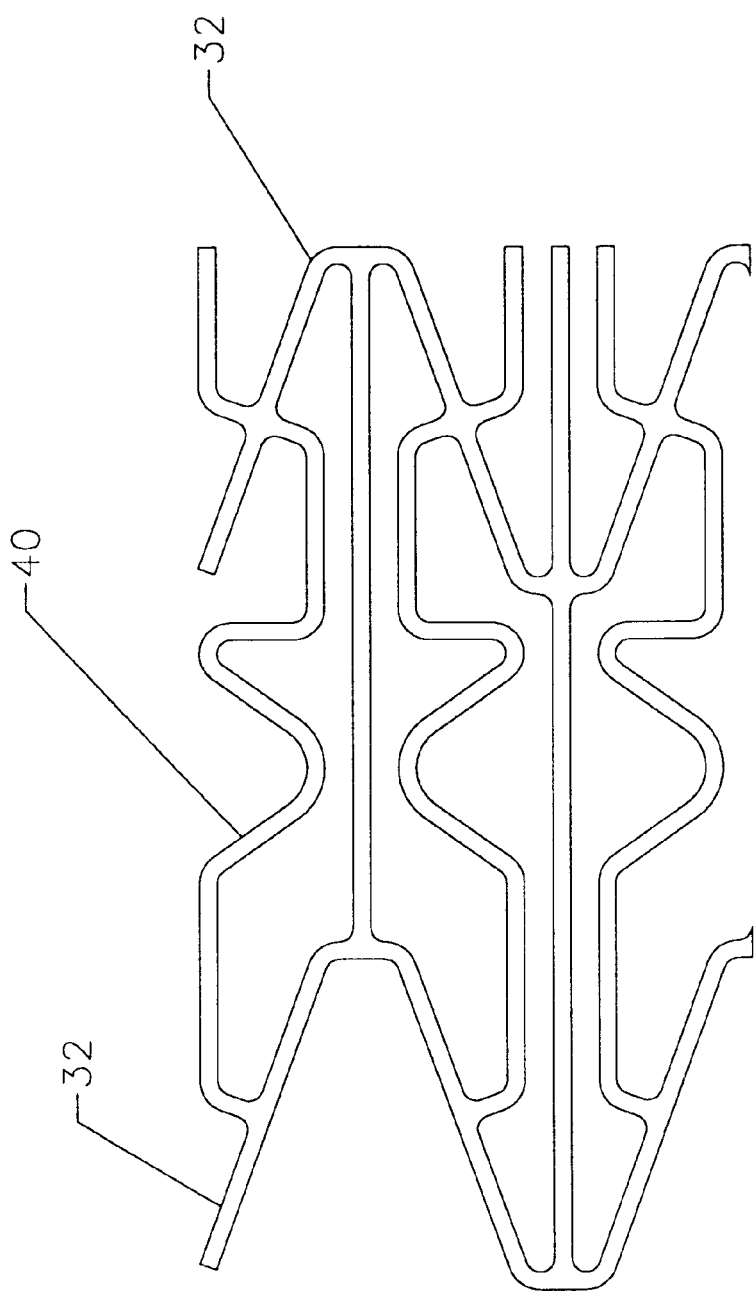
FIG. 5 depicts in greater detail the articulated arms of the stent shown in FIG. 4.

FIG. 5 depicts in greater detail the interconnection of the cylindrical elements 32 by the connecting arms 34 and substantially straight connecting rods 38. As shown in FIG. 5, the cylindrical elements 32 can be joined at their midpoint to the articulated arms 34 which extend between adjacent pairs of cylindrical elements 32. Additionally, FIG. 5 depicts that the connecting rods 38 can extend between the trough portions of the U-shaped elements of the cylindrical elements 32.

FIG. 5 shows in greater detail each of the articulated arms 34. In particular, FIG. 5 shows that each articulated arm 34 includes a curved section 40. The curved section 40 provides additional scaffold for the stent 30, and therefore provides increased coverage of the interior tissue wall of the body lumen. This increased coverage is understood, inter alia, to reduce the likelihood that loose tissue from the lesion will extend into the interior of the stent. This is understood to reduce the chance of restenosis caused by thrombosis which can form around the loose tissue. FIG. 5 depicts one embodiment of curved section for providing the stent with additional scaffold, however other geometries and patterns can be employed. For example, the curved section 40 can include S-shaped sections, or straight sections. Additionally, it will be understood that the geometry of the connecting rods 38 or the sinusoidal coils can also be altered to increase the scaffold density of the stent's peripheral wall.

In the depicted embodiment, each U-shaped element of each cylindrical elements is connected to an adjacent U-shaped member of an adjacent cylindrical elements by a pair of articulated arms, and by a connecting rod. However, as described above with reference to FIGS. 1 through 3, it will be understood that other techniques and patterns for connecting adjacent U-shaped elements can be practiced with the invention. For example, alternating pairs of adjacent U-shaped elements can be connected by the articulated arms 40. Moreover, these alternating pairs of articulated arms can be staggered between adjacent pairs of joined sinusoidal coils. Other techniques for interconnecting the sinusoidal coils for stents which include articulated arms and substantially straight connecting rods can be practiced without departing from the scope thereof.

While there have been shown and described what are at present considered the preferred embodiments of the invention, it will be obvious to those skilled in the art that various changes and modifications may be made therein without departing from the scope of the invention as defined by the appended claims. These other modifications can include stent-graft devices, wherein a graft is disposed around the periphery of the stent. The graft can be a biocompatible sheath of material, such as polyester or PTFE. The design of such grafts is known in the art, and any suitable graft can be employed herewith. Additionally, the stents described herein can include stents that include sidewall apertures for forming bifurcated stents.

I claim:

1. An intraluminal stent for implanting in a body lumen, comprising:

a first cylindrical element adapted for expanding from a first radial dimension to a second radial dimension;

a second cylindrical element adapted for expanding from a first radial dimension to a second radial dimension, and being positioned adjacent and spaced away from the first cylindrical element to define a longitudinal axis extending through the first and second cylindrical elements;

an articulated arm connecting the first and second cylindrical elements; and a substantially straight connecting rod connecting the first and second cylindrical elements, wherein said first cylindrical element comprises a coil having a plurality of peaks and troughs and the articulated arm joins the first and second cylindrical elements at a point on the coil of said first cylindrical element at a location between a peak and a trough, whereby a force acting radially outward may expand the stent from the first radial dimension to the second radial dimension.

2. An intraluminal stent according to claim 1, wherein the articulated arm further comprises a section adapted for providing increased coverage of the body lumen tissue wall.

3. An intraluminal stent according to claim 2, wherein the expansion section comprises a curved section of deformable material.

4. An intraluminal stent according to claim 1, wherein the first and second cylindrical elements each comprise a serpentine coil having a plurality of peaks and troughs and wherein the connecting rod extends between a peak on the first cylindrical element and a peak on the second cylindrical element.

5. An intraluminal stent according to claim 1, further comprising a graft formed about a surface defined by the first and second cylindrical elements.

6. An intraluminal stent according to claim 1, wherein the overall length of the stent in the first radial dimension is substantially the same as the overall length of the stent in the second radial dimension.

7. An intraluminal stent according to claim 1, wherein the stent is formed from a substantially tubular body of material.

8. An intralurninal stent according to claim 1, wherein the stent is formed from a substantially flat sheet of material.

9. An intravascular stent according to claim 1, further comprising a plurality of articulated arms and connecting rods extending between the first and second cylindrical elements, thereby defining an exterior surface having apertures therethrough.

10. An intravascular stent according to claim 9, wherein the apertures of the exterior surface are dimensionally adapted to provide wall support.

* * * * *

UNITED STATES PATENT AND TRADEMARK OFFICE
CERTIFICATE OF CORRECTION

PATENT NO.   : 6,066,169
DATED        : May 23, 2000
INVENTOR(S)  : Colm P. McGuinness It is certified that error appears in the above-identified patent and that said Letters Patent is hereby corrected as shown below:

Title page,
Item [56], References Cited, U.S. PATENT DOCUMENTS, add -- 5,718,713 02/1998 Frantzen --
FOREIGN PATENT DOCUMENTS, add
-- WO 97/3254 09/1997 WIPO
  EP 0 875 215 11/1998 European Patent Office
  EP 0 887 051 12/1998 European Patent Office --

Column 1,
Line 61, delete "falls" and insert -- fails -- therefor.

Column 2,
Line 1, delete "falls" and insert -- fails -- therefor.

Column 4,
Line 63, delete "coil 12 has".

Column 5,
Line 1, delete "elements" (both occurrences) and insert -- element -- therefor.
Line 2, delete "calendrical" and insert -- cylindrical -- therefor.
Lines 5 and 13, delete "elements" and insert -- element -- therefor.

Column 6,
Lines 62-63, delete "sinu-soidal"
Lines 66-67, delete "elements" and insert -- element --therefor.

UNITED STATES PATENT AND TRADEMARK OFFICE
CERTIFICATE OF CORRECTION

PATENT NO.    : 6,066,169
DATED         : May 23, 2000
INVENTOR(S)   : Colm P. McGuinness It is certified that error appears in the above-identified patent and that said Letters Patent is hereby corrected as shown below:

<u>Column 7,</u>
Lines 41 and 42, delete "elements" and insert -- element -- therefor.

Signed and Sealed this

Ninth Day of September, 2003

JAMES E. ROGAN
*Director of the United States Patent and Trademark Office*